United States Patent
Zwyer

(10) Patent No.: US 11,596,622 B2
(45) Date of Patent: Mar. 7, 2023

(54) MAZINDOL TREATMENT FOR HEROIN DEPENDENCE AND SUBSTANCE USE DISORDER

(71) Applicant: NLS Pharmaceutics AG, Stans (CH)

(72) Inventor: Alexander C. Zwyer, Teufen (CH)

(73) Assignee: NLS Pharmaceutics AG, Stans (CH)

( * ) Notice: Subject to any disclaimer, the term of this patent is extended or adjusted under 35 U.S.C. 154(b) by 97 days.

(21) Appl. No.: 16/645,306

(22) PCT Filed: Sep. 6, 2018

(86) PCT No.: PCT/IB2018/001138
§ 371 (c)(1),
(2) Date: Mar. 6, 2020

(87) PCT Pub. No.: WO2019/058172
PCT Pub. Date: Mar. 28, 2019

(65) Prior Publication Data
US 2021/0161865 A1 Jun. 3, 2021

Related U.S. Application Data

(60) Provisional application No. 62/555,469, filed on Sep. 7, 2017.

(51) Int. Cl.
*A61K 31/4184* (2006.01)
*A61P 25/36* (2006.01)
*A61K 9/24* (2006.01)

(52) U.S. Cl.
CPC .......... *A61K 31/4184* (2013.01); *A61K 9/209* (2013.01); *A61P 25/36* (2018.01)

(58) Field of Classification Search
CPC ...... A61K 9/209; A61K 31/4184; A61P 25/36
See application file for complete search history.

(56) References Cited

U.S. PATENT DOCUMENTS

| | | | | |
|---|---|---|---|---|
| 5,217,987 A * | 6/1993 | Berger | ............... | A61K 31/00 514/255.04 |
| 2013/0011483 A1* | 1/2013 | Kidane | ............... | A61K 31/4184 424/490 |
| 2013/0273162 A1 | 10/2013 | Li | | |

FOREIGN PATENT DOCUMENTS

| | | |
|---|---|---|
| JP | 2003-504303 | 2/2003 |
| WO | WO 91/11184 A1 | 8/1991 |
| WO | WO 2011/123496 | 10/2011 |
| WO | WO 2017/153846 | 9/2017 |

OTHER PUBLICATIONS

International Search Report from the European Patent Office in corresponding International Application No. PCT/IB2018/001138 dated Feb. 22, 2019.
Written Opinion of the International Searching Authority from the European Patent Office in corresponding International Application No. PCT/IB2018/001138 dated Feb. 22, 2019.
Tatsumi et al., Pharmacological profile of antidepressants and related compounds at human monoamine transporters; European Journal of Pharmacology 340 (1997), pp. 249-258.
Napier et al., Using conditioned place preference to identify relapse prevention medications; Neuroscience and Biobehavioral Reviews 37 (2013), pp. 2081-2086.
U.S. Department of Health and Human Services, Food and Drug Administration, Center for Drug Evaluation and Research (CDER); Guidance for Industry; Estimating the Maximum Safe Starting Dose in Initial Clinical Trials for Therapeutics in Adult Healthy Volunteers (2005).

* cited by examiner

*Primary Examiner* — Theodore R. Howell
(74) *Attorney, Agent, or Firm* — Finnegan, Henderson, Farabow, Garrett & Dunner, L.L.P.

(57) ABSTRACT

The present invention relates to mazindol for use in the treatment of dependence and substance use disorder, wherein the substance is an opioid, a composition comprising mazindol and optionally a pharmaceutically acceptable carrier or excipient and/or a diluent, for use in the treatment of substance abuse disorder, wherein the substance is an opioid, and a method of treatment of substance abuse disorder comprising administering mazindol or composition comprising mazindol to a subject, wherein the substance is an opioid. The opioid is preferably heroin.

9 Claims, 7 Drawing Sheets

MAZINDOL TREATMENT FOR HEROIN DEPENDENCE AND SUBSTANCE USE DISORDER

This application is a national stage filing under 35 U.S.C. § 371 of International Application No. PCT/IB2018/001138, filed on Sep. 6, 2018, which claims priority of U.S. Provisional Application No. 62/555,469, filed on Sep. 7, 2017. The contents of these applications are each incorporated herein by reference.

CLAIM FOR PRIORITY

This PCT International Application claims the benefit of priority of U.S. Provisional Patent Application No. 62/555,469, filed Sep. 7, 2017, the subject matter of which is incorporated herein by reference in its entirety.

FIELD OF THE INVENTION

The present invention relates to use of mazindol in treatment for opioid dependence and substance use disorder, and a method of treatment in opioid dependence and substance use disorder.

BACKGROUND OF THE INVENTION

Heroin is an opioid drug made from morphine which binds to $\mu$-opioid, $\kappa$-opioid and $\delta$-opioid receptors. Prolonged use of psychoactive substances over time may lead to dependence and/or substance use disorder. Psychoactive substances which are commonly used as recreational drugs include alcohol, cocaine, amphetamines related-derivatives and opioid substances. Any substance which increases pleasure-reward signaling in the mesocorticolimbic system of the brain may precipitate synaptic changes which lead to long term behavioral changes, such as addictive-type behavior.

The impact of substance use disorder on society is both harmful and costly. In 2015, substance abuse cost US society $249 billion for alcohol and $193 billion for illegal drugs (1). These costs relate to healthcare, crime and loss of work productivity. Specifically, opioid overdose, abuse and dependence related behavior alone cost the US $78.5 billion in 2009 (2).

Methods currently used to treat substance use disorder include maintenance therapy or detox whereby a substitute drug, such as methadone for heroin dependence and addiction, is provided. The dosage may be tapered until the substitute drug is no longer administered. Therapy and behavioral counselling are also used to treat substance abuse disorders Pharmacological intervention such as the administration of anti-anxiolytics and anti-depressants may also be used as part of the treatment of substance use disorder in order to reduce withdrawal symptoms. Once a subject begins to abstain from or reduce administration of a substance, withdrawal symptoms are commonly present. Withdrawal symptoms can be highly uncomfortable, and in some cases, fatal. Symptoms include irritability, anxiety, sweating, nausea, vomiting, diarrhea, fatigue, tremors, headache, insomnia and loss of concentration. In severe cases, hallucinations, seizures and death are possible.

Relapse is also common in those who suffer from substance use disorder. Relapse occurs when a subject returns to administering the substance of abuse after a period of abstinence from the substance. Unfortunately, abstinence or a reduction in the dose of a substance can reduce a subject's tolerance to that substance, whilst the cravings remain the same. Therefore when relapse occurs, a subject may administer an amount which satisfies the craving, but may be harmful and even lethal due to reduced physiological tolerance.

Methadone is a synthetic opioid compound used as a heroin replacement in treating substance use disorder. However, dependency can arise and it is not uncommon for subjects to abuse methadone in the same way as other opioids such as heroin. Side effects of methadone use include anxiety, insomnia, drowsiness, nausea, vomiting, diarrhea, respiratory depression and hypotension. Methadone has been implicated in a number of lethal overdoses, especially when mixed with other drugs such as alcohol, benzodiazepines and cocaine.

Naltrexone is a $\mu$-opioid, $\kappa$-opioid and a $\delta$-opioid receptor antagonist. It can be used to prevent the euphoria experienced by opioid use, and in turn eventually reduce the cravings in users who exhibit signs of opioid abuse. It has also been used to treat alcohol addiction. However, it is only recommended for use in treating substance use disorder when an initial period of abstinence from opioids has been achieved. This is to avoid acute harmful withdrawal symptoms from opioid abuse.

Buprenorphine is a partial opioid agonist that relieves drug cravings without producing the "high" or dangerous side effects of other opioids. Buprenorphine is also available in combination with naloxone (an opioid antagonist) and can be taken orally or sublingually to avert withdrawal symptoms with naloxone.

A vaccine comprising an optimized heroin-tetanus toxoid immune-conjugate has also been developed in order to treat opioid substance use disorder (3). Preclinical studies have demonstrated that this vaccine is able to reduce the euphoric effects of heroin, thereby suggesting it may be a viable treatment for preventing the craving aspect of opioid addiction. However, the vaccine is in preclinical testing and has not yet been approved for use in humans.

Therefore, there is a need for a treatment for substance use disorder, specifically opioid abuse disorder, which obviates the problems associated with current treatments such as methadone and naltrexone administration. These problems include addiction to the substance which is being used to treat the substance abuse, managing uncomfortable and harmful withdrawal effects, and relapse. Furthermore, a treatment which is currently approved for use in humans and which can be administered within an acute stage of withdrawal would be advantageous.

Mazindol has been investigated as a potential candidate in treating cocaine addiction (6). However, subsequent studies have reported mazindol as being ineffective at treating cocaine abuse and dependence (7, 8). The rate of relapse, number of days to relapse and cocaine use in these studies did not differ between subjects who were given mazindol and subjects who were given a placebo.

Mazindol is a psychopharmacologic agent different from that of currently available wake-promoting drugs and psychostimulants and has a receptor signature and functional activity profile different from those of available attention deficit/hyperactivity disorder (ADHD) treatments such as d-amphetamine, which is a moderately potent inhibitor of dopamine transporter, norepinephrine transporter and vesicular monoamine transporter 2 with weaker affinities for serotonin transporter. Currently available psychostimulants (e.g. amphetamine salts) may lead to substance use disorders and discontinuation due to a decline in efficiency (e.g. in adults), but none of them promote a regulator effect on opioid addiction.

Use of mazindol when administered intraperitoneally (i.p.) has also been investigated for its effects on spontaneous pain related behaviors (12).

Use of mazindol in treatment of attention deficit/hyperactivity disorder (ADHD) has been described in U.S. Pat. No. 8,293,779. It is considered, in current medication classifications, as a psychoanaleptic and anorexigenic medication. It is currently authorized in Argentina, Mexico/Central America, and Japan for use in the treatment of obesity. Mazindol is a non-amphetamine compound because of its tricyclic chemical structure. It offers a pharmacological profile very close to that of amphetamines with less abuse liability. Indeed, mazindol is not metabolised to an amphetamine-like compound. The Met (2-(2-Aminoethyl)-3-(p-chlorophenyl)-3-hydroxyphthalimidine) has been identified to be the main metabolite of mazindol in man (Dugger et al., 1979). Met has been found to result from the hydrolysis of mazindol at moderate temperatures in neutral and alkaline aqueous solutions (Nakashima et al., 2004). Both mazindol and Met exhibit very close pharmacological properties. Mazindol and its metabolite act by blocking dopamine and norepinephrine reuptake similarly to amphetamines, but have a higher affinity for μ-opioid receptors and a modest affinity for κ-opioid receptors.

Table A discloses mazindol and Met tested at $1.0 \times 10^{-0.5}$ M and the compound binding calculated as a percent inhibition of the binding of a radioactively labeled ligand specific for each target (Eurofins CEREP, France).

TABLE A

Test compound manufacturer information

| Compound ID | Batch Number | FW | MW | Purity | Formulation | Stock Solution |
|---|---|---|---|---|---|---|
| Mazindol (100028703-1) | ACVH001 | 284.74 | | 99.0 | Powder | $1 \times 10^{-02}$M DMSO |
| Mazindol metabolite (100028703-3) | ACBA416 | 339.26 | 339.26 | 92.0 | Powder | $1 \times 10^{-02}$M DMSO |

FW: Formula Weight;
MW: Molecular Weight

An inhibition or stimulation of more than 50% is considered a significant effect of the test compounds. Fifty percent is a common cut-off for further investigation (i.e. determination of $IC_{50}$ or $EC_{50}$ values from concentration-response curves). Tables B and C display the binding profiles for Mazindol and Met.

TABLE B

Compound Mazindol bindng activity

| Assay | $1.0 \times 10^{-05}$ M |
|---|---|
| 5-HT transporter(h)[a] | 99.5% |
| 5-HT$_{1A}$(h)[b] | 89.5% |
| 5-HT$_7$(h)[b] | 52.9% |
| Dopamine transporter(h)[a] | 98.2% |
| H$_1$(h)[a] | 75.3% |
| M$_1$(h)[a] | 52.1% |
| μ (MOP) (h)[b] | 89.9% |

TABLE B-continued

Compound Mazindol bindng activity

| Assay | $1.0 \times 10^{-05}$ M |
|---|---|
| Norepinephrine transporter (h)[a] | 100.4% |

[a]antagonist radioligand
[b]agonist radioligand

TABLE C

Compound Mazindol Metabolite binding activity

| Assay | $1.0 \times 10^{-05}$ M |
|---|---|
| 5-HT transporter(h)[a] | 98.5% |
| 5-HT$_{1A}$(h)[b] | 86.3% |
| Dopamine transporter(h)[a] | 101% |
| H$_1$(h)[a] | 75.5% |
| k (KOP)[b] | 53.3 |
| M$_1$(h)[a] | 50.4% |
| μ (MOP) (h)[b] | 87.9% |
| Norepinephrine transporter (h)[a] | 100.2% |

[a]antagonist radioligand
[b]agonist radioligand

The results are expressed as a percent of control specific binding obtained in the presence of the test compounds:

$$\frac{\text{Measured specific binding}}{\text{Control specific binding}} \times 100$$

and as a percent inhibition of control specific binding obtained in the presence of the test compounds:

$$100 - \left(\frac{\text{Measured specific binding}}{\text{Control specific binding}} \times 100\right)$$

The IC50 values (concentration causing a half-maximal inhibition of control specific binding) and Hill coefficients (nH) were determined by non-linear regression analysis of the competition curves generated with mean replicate values using Hill equation curve fitting:

$$Y = D + \left[\frac{A - D}{1 + (C/C_{SD})^{nH}}\right]$$

where Y=specific binding, A=left asymptote of the curve, D=right asymptote of the curve, C=compound concentration, C50=IC50, and nH=slope factor. This analysis was performed using software developed at Cerep (Hill software) and validated by comparison with data generated by the commercial software SigmaPlot® 4.0 for Windows® (©1997 by SPSS Inc.).

The inhibition constants (Ki) were calculated using the Cheng Prusoff (1973) equation:

$$K_i = \frac{IC_{50}}{(1 + L/K_D)}$$

where L=concentration of radioligand in the assay, and KD=affinity of the radioligand for the receptor. A scatchard plot was used to determine the KD.

In addition, in animal toxicology studies, the toxic potential of mazindol has proved to be very low. In particular, no carcinogenic effect, no mutagenic effect, and no toxicology effect in reproduction was observed. In U.S. Pat. No. 8,293, 779, it is disclosed that, after single or repeated oral administration, mazindol is absorbed with a time to maximum concentrations (Tmax) of 2-4 hours. The half-life time of mazindol after an immediate release formulation is 9.1±1.7 h in healthy volunteers (Kim 2009); therefore, steady-state concentrations are reached after approximately 30-55 hours. The pharmacokinetics is linear (independent of the dose) between 1 mg/day and 4 mg/day. This result however relates to current immediate release formulations of mazindol. Immediate-release pharmaceutical compositions of mazindol, such as Diminex®, Sanorex® and Teronac®, ensure the release of the active ingredient over a period of <1 h in vitro. Indeed, immediate-release pharmaceutical compositions of mazindol have been reported to undergo hydrolysis at moderate temperatures in neutral and alkaline aqueous solutions, including in human plasma. Due to the mild alkaline nature of plasma, improved mazindol stability in human plasma is achieved by adding acidic buffer.

To achieve once daily dosing regimen (a very desirable regimen for compliance), a better controlled release portion would also be needed to assure that adequate plasma concentrations are achieved throughout the day and evening, while also allowing the subject to fall asleep and remain asleep during the night. Thus, there is a need for a pharmaceutical composition with an improved release profile of active substance combining an immediate and a sustained release, an improved compliance for patients, and reduced fluctuation in steady-state plasma concentrations during a dosing interval, for treatment of a substance use disorder.

The above mentioned problems have been solved by the aspects and embodiments of the present invention outlined below.

SUMMARY OF THE INVENTION

The present invention provides mazindol for use in the treatment of substance use disorder. Preferably, the substance is an opioid.

The present invention also provides a method of treatment of substance use disorder, wherein the substance is an opioid, comprising administering mazindol to a subject.

The present invention also provides a composition comprising mazindol for use in a method of the treatment of opioid abuse disorder or pain, when in the form of a multi-layer matrix type tablet comprising:

at least one immediate-release (IR) layer comprising mazindol and at least one diluent, and at least one sustained release (SR) layer comprising mazindol and at least one sustained release, pH independent and water-insoluble polymer.

in accordance with the present invention, mazindol is effective at treating opioid substance use disorder by reducing both opioid rewarding effect and withdrawal symptoms.

A bilayer tablet comprising mazindol which exhibits an improved release profile is described in Application No. 62/305,600 and PCT/EP2016/055048, which are hereby incorporated by reference in their entirety. The oral pharmaceutical unit dosage form of mazindol in the form of a multilayer matrix-type tablet of the invention provides a rapid release portion to provide a continual release of mazindol available for absorption into the patients' blood stream to achieve a prolonged therapeutic effect. This combination can thus achieve a once daily regimen for the product. This therefore has the following advantages:

Ease of swallowing;

Ease of manufacture;

The ability to control the release rate of the drug by modifying the components of each separate layer;

Superior stability compared to other dose forms, such as capsules, liquids;

Prevents patient tampering with the dose form;

Reduced fluctuation in steady-state mazindol plasma concentrations during a dosing interval;

Enhanced stability;

Onset within 1-2 hours, while not unnecessarily delaying consumption of food; and Muted increase in heart rate.

DETAILED DESCRIPTION OF THE INVENTION

Figure 1:
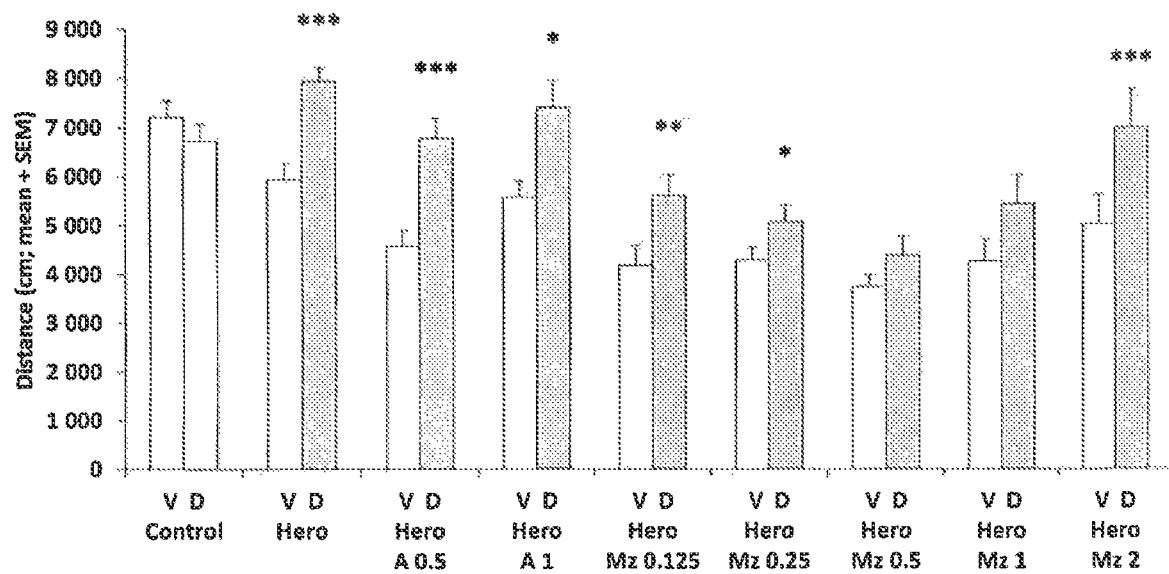
FIG. 1 shows (higher panel) and compares (lower panel) the distance travelled in a vehicle-paired (V) and in a drug-paired (D) compartment after administration with a control, mazindol or amphetamine in mice.
Figure 1:
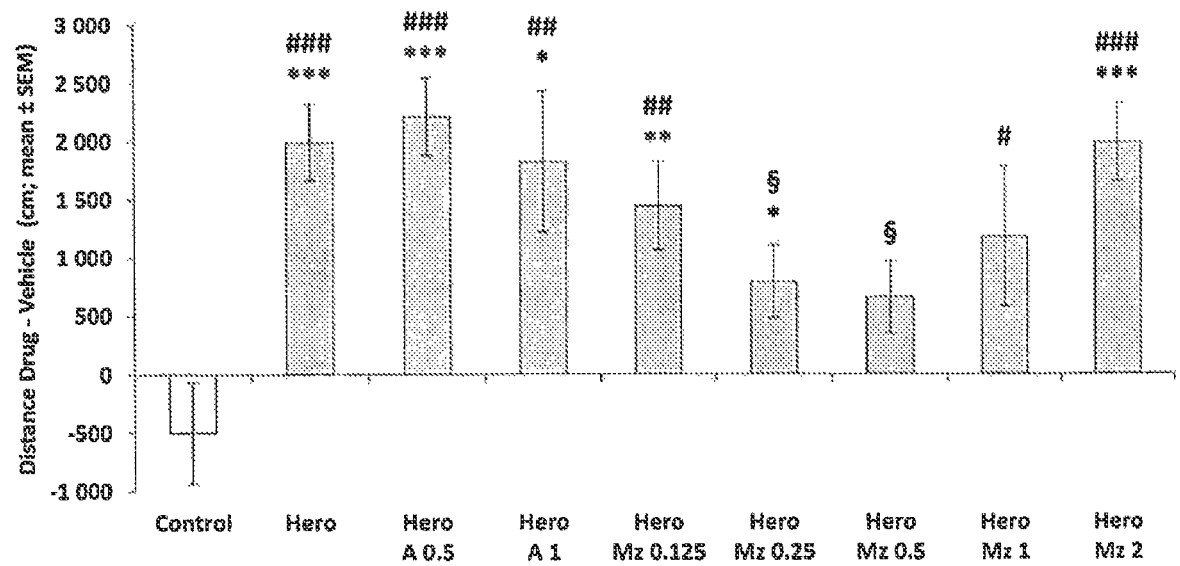

Mazindol (5-(4-chlorophenyl)-2,5-dihydro-3 H-imadazo[2,1-a]isoindol-5-ol) has the following chemical formula:

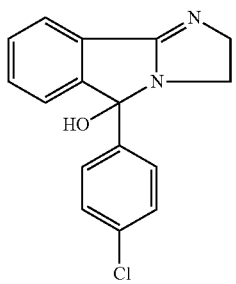 [SMILES: OC1(c2ccc(Cl)cc2)c2ccccc2C2=NCCN21]

The term "substance use disorder" as used in the present application refers to any stages associated with administration of, addiction to and withdrawal from a substance of abuse. This includes craving a substance, administering the substance and experiencing euphoria (a high), contentment or relaxation. When abstinent from the substance the subject may experience irritability, anxiety, sweating, nausea, vomiting, diarrhea, fatigue, tremors, headache, insomnia, loss of concentration, hallucinations, seizures and increased cravings, These are also known as withdrawal symptoms.

The term "dependence" as used in the present application refers to any stages associated with prolonged use of a substance of use. This can include stages within the term "substance use disorder" and may include craving a substance, administering the substance in order to reduce or stop the craving, and when abstinent from the substance the subject may experience any of the above withdrawal symptoms.

A subject with a substance use disorder may or may not be exhibiting behaviour associated with abuse and dependence.

Substances of abuse and dependence include, but are not limited to, opioids (such as heroin, opium, morphine, buprenorphine, codeine, fentanyl, hydrocodone, methadone, tramadol, and any naturally occurring or synthetic derivatives or related compounds thereof) alcohol, cocaine, crack cocaine, amphetamines, methamphetamines, benzodiazepines, GHB and nicotine.

A subject may be using, or addicted to, more than one opioid or other substances of abuse and dependence simultaneously.

The use of the compounds and compositions of the present invention are suitable for all mammals and particularly humans.

Mazindol may be used simultaneously alongside other treatments for substance use disorder, such as methadone, buprenorphine/naloxone, and/or naltrexone administration, anti-anxiolytic administration and counselling.

The present invention also provides mazindol for use in the treatment of pain, preferably rheumatic pain. The pain may be neuropathic or nociceptive pain. The pain may be acute or chronic.

Mazindol is preferably administered to a subject orally in the form of a tablet or capsule. Mazindol may also be administered or used as a liquid or powder formulation. The administration of or use of mazindol may be wherein mazindol is suitable for injection or infusion, via an intravenous, subcutaneous, subdermal, intraperitoneal or intraocular route. Mazindol is preferably administered in a formulation with a sustained release, such as the bilayer tablet described herein.

The tablet, or oral pharmaceutical unit dosage form, in preferably in the form of a multilayer matrix-type tablet can provide a rapid release of drug to achieve a rapid therapeutic blood level and a sustained release portion to provide a continual release of mazindol available for absorption into the patients' blood stream to achieve a prolonged therapeutic effect.

The term "matrix-type tablet" is used in the invention to designate a tablet whose inner structure in each layer is homogeneous and identical from the center towards the periphery of the layer. Therefore, the layers of the tablets of the present invention consist of a homogeneous mixture of active ingredient in powder or granule form and of a compression matrix.

An "immediate-release (IR) layer" refers to a layer that releases greater than or equal to about 80% by weight of mazindol in less than or equal to about 1 hour. A "sustained-release (SR) layer" means a layer in which mazindol is released at a rate slower than that of an IR layer. The ratio in weight between the IR layer/s and the SR layer/s of such a tablet is preferably between 40:60 and 80:20, more preferably between 50:50 and 70:30, most preferably 50:50.

A process for preparing the tablet may comprise the following steps:
(a) preparing a blend of IR layers
(b) preparing a blend of SR layers
(c) adding the IR blend of step (a) and the SR blend of step (b) into a multilayer, preferably a bilayer, tablet press.

Mazindol for any of the embodiments described above may also be provided in a composition comprising additional components including a pharmaceutically acceptable carrier or excipient, or diluent.

Examples of diluents include: lactose, monohydrate lactose, anhydrous lactose, spray-dried lactose, calcium carbonate, calcium sulfate, calcium sulfate dehydrate, calcium lactate trihydrate, monobasic calcium sulfate monohydrate, calcium carbonate, tribasic calcium phosphate, diabasic calcium phosphate, compressible sugars, dextrates, dextrin, dextrose, calcium phosphate, kaolin, magnesium carbonate, magnesium oxide, maltodextrin, mannitol, powdered cellulose, starch, modified starch, starch hydrolyzates, pregelatinized starch, microcrystalline cellulose, powdered cellulose, cellulose and cellulose derivatives, hydroxypropylmethylcellulose, hydroxypropylmethylcellulose and sucrose, preferably lactose, anhydrous lactose, spray-dried lactose, microcrystalline cellulose, powdered cellulose, cellulose and cellulose derivatives.

Diluent concentration in the composition or IR layer of a multilayer tablet can be varied between 1 and 95%, preferably 30 and 60%, more preferably 45 to 55% by weight of the total weight of the composition, or the IR layer in a multi-layer matrix type tablet.

Preferably, a unit dosage form according to the invention comprises a lubricant in the composition or tablet layer. Lubricants and glidants can be employed in the present invention to prevent, reduce or inhibit adhesion or friction of ingredients of the composition. They facilitate the compression and ejection of compressed compositions from a desired die. They are compatible with the ingredients of the pharmaceutical composition, and they do not significantly reduce the solubility, hardness, chemical stability, physical stability, or the biological activity of the pharmaceutical composition. The pharmaceutically acceptable lubricants and glidants for the present invention are selected from the group including but not limited to stearic acid, metallic stearates, zinc stearate, magnesium stearate, magnesium trisilicate, calcium hydroxide, tribasic calcium phosphate, magnesium carbonate, magnesium oxide, calcium stearate, glyceryl monostearate, waxes, glycerides, glyceryl behenate, glyceryl palmitostearate, silicone oil, hydrogenated vegetable oil, hydrogenated castor oil, light mineral oil, mineral oil, polyethylene glycol, methoxypolyethylene glycol, sodium acetate, sodium oleate, sodium chloride, leucine, sodium benzoate, alkyl sulfates, sodium lauryl sulfate, sodium stearyl fumarate, talc, colloidal silica, corn starch, powdered cellulose, and/or boric acid. The preferred range of lubricants/glidants is from 0% to 1% w/w of the composition or tablet layer.

Sustained-release, pH-independent and water-insoluble polymers can also be used in the composition or SR layers of the tablets according to the invention is selected in the group consisting of cellulose polymers, high-molecular-weight polymers of acrylic acid that are crosslinked with either allyl sucrose or allyl ethers of pentaerythritol (Carbopol, Carbomers), polymers from the class of methacrylic acids, polyvinylalcohol derivatives, polymers of lactic and glycolic acids (PLGA), starches, waxes, polyvinyl acetate derivatives, polyvinyl pyrrolidone derivatives and mixtures thereof, preferably is selected in the group consisting of cellulose polymers and high-molecular-weight polymers of acrylic acid that are crosslinked with either allyl sucrose or allyl ethers of pentaerythritol (Carbopol, Carbomers). Cellulose polymers include hydroxypropyl methylcellulose (HPMC), hydroxypropyl cellulose (HPC), sodium CMC, ethyl cellulose derivatives such as cellulose acetate, cellulose acetate butyrate, cellulose acetate cellulose propionate, hydroxypropylmethylcellulose acetate succinate, microcrystalline cellulose (for example such as the one supplied under the trade mark Avicel®, and ethylcellulose (for example the one supplied under the trade mark Aqualon® ethylcellulose).

Polymers from the class of methacrylic acids include the grades Eudragit®RL 12.5, RL PO and RL 100 and RS 12.5, RS PO and RS 100. Starches include natural starches e.g. corn starches and modified starches such as pre-gelled starch. Waxes include white or yellow beeswax, polyvinyl acetate derivatives.

Sustained-release, pH-independent and water-insoluble polymer concentration in the composition or SR layers of a multilayer tablet can be varied between 80 and 99%, preferably 90 to 97% by weight of the total weight of the composition or SR layers.

The tablet form according to the invention can include anti-agglomerant agents. Anti-agglomerant agents used in the present invention include talc, silicon dioxide and its derivatives, acrylic esters, castor oil derivative, cellulose compounds, iron oxides, magnesium stearate, stearic acid and or sodium stearate.

Layers of a tablet according to the present invention can comprise a binder. Binders according to the invention, include hydroxypropylmethylcellulose (HPMC), hydroxypropylcellulose (HPC), maltodextrin, polyvinylpyrrolidone (PVP) and or microcrystalline cellulose.

As described herein, a controlled release formulation of mazindol is provided containing immediate and sustained release layers in a layered tablet, which when ingested leads to an initial burst of mazindol followed by a slower, continual release, for example, over 6-8 hours (from ingestion) where it can be dissolved and absorbed in the small intestine, before it reaches the colon.

The initial availability of mazindol is advantageous for patients because they need a sufficient drug levels at the beginning of their day. Subsequently, the slower continual release and absorption of mazindol in the intestine provided by the formulation of the present invention assures that adequate plasma concentrations are achieved throughout the day and evening, while allowing the subject to fall asleep and remain asleep during the night.

Mazindol or a composition comprising mazindol, while not especially limited can be administered daily to a subject. A daily dosage may range from 0.25 mg to 16 mg, preferably 1 to 9 mg and more preferably 1 mg to 3 mg.

The present invention will now be illustrated, but in no way limited, by reference to the following examples.

EXAMPLES

Conditioned place preference (CPP) is a widely used procedure for studying the potential addictive effect of drugs. CPP is based upon the tendency of rodents to approach a stimulus that has previously been paired with an incentive state induced by a drug. A drug that induces a CPP may be suspected to present reinforcing effects that could lead to addiction. Numerous addictive drugs, such as opiate agonists or stimulants induce a CPP and a behavioral sensitization.

The abrupt cessation of chronic opiate use results in a well characterized withdrawal syndrome with symptoms that include pain sensitivity, dysphoria, irritability, restlessness, insomnia, diarrhea and hyperventilation. In the present model, the naloxone-precipitated withdrawal syndrome is measured in rodents. Animals are chronically treated with a drug, e.g. morphine or heroin. Opiate withdrawal syndrome is elicited by an acute injection of the opiate antagonist Naloxone.

Past studies using similar experimental procedures have shown that morphine induced place preference in C57BL/6J mice and opioid withdrawal syndrome following naloxone injection in Sprague-Dawley rats.

The effect of mazindol on place preference was examined in C57BL/6J mice using a method similar to the one used by Schlussman et al. (9).

The effect of mazindol on heroin withdrawal syndrome elicited by naloxone was examined in Sprague-Dawley rats using a method similar to the one used by Jiang et al. (10), In the present study, the effect of mazindol was compared with those of methylphenidate and D-amphetamine.

Here, mazindol has been tested in two rodent models which account for two components of addiction, the CPP paradigm which is widely used to measure the rewarding effect of a drug, and the heroin withdrawal symptoms precipitated by naloxone. These two components, the rewarding effect and the withdrawal symptoms, contribute to the craving for drug of abuses such as heroin.

The study included five experiments. The first four experiments were performed on mice. The fifth experiment was performed on rats. The first experiment consisted in determining the doses of mazindol, D-amphetamine and methylphenidate which are devoid of significant motor effects that might disrupt the measure of place preference. For this purpose, the effects of mazindol and D-amphetamine on spontaneous locomotor activity were examined in mice.

The second experiment consisted in determining the optimal dose of heroin which induces the most significant CPP. For this purpose, the CPP induced by heroin at 1.25, 2.5 and 5 mg/kg was examined.

The third experiments consisted in examining the effects of mazindol and D-amphetamine (at doses chosen from results of the first part of the study) on the place preference induced by heroin at a dose chosen from results of the second experiment, which was 1.25 mg/kg. Mazindol (0.125, 0.25 and 0.5 mg/kg) and D-amphetamine (0.5 mg/kg) were tested.

The results of experiment 3 showed that mazindol (0.25 and 0.5 mg/kg) tended to reduce the place preference induced by heroin. Therefore, it was decided to perform an additional experiment to examine the effects on place preference induced by heroin of mazindol at 1 and 2 mg/kg and of D-amphetamine at 1 mg/kg. It was also decided to examine in the same experiment whether mazindol (2 mg/kg) induced a place preference.

The fifth experiment consisted in examining the effects of mazindol and D-amphetamine on physical heroin withdrawal symptoms induced by naloxone.

The first experiment led to select the doses of 0.125, 0.25 and 0.5 mg/kg for mazindol and the dose of 0.5 mg/kg for D-amphetamine. It also led to choose pretreatment times of 60 min for mazindol and 30 min for D-amphetamine.

The second experiment showed the heroin induced CPP at the three doses tested and that 1.25 mg/kg was suitable to examine the effects of treatments on CPP.

The third and fourth experiments showed that mazindol (0.25, 0.5 mg/kg), but not D-amphetamine (0.5, 1 mg/kg), decreased the place preference induced by heroin.

The fifth experiment showed that mazindol at doses of 0.25, 0.5, 1 and 2 mg/kg reduced the withdrawal symptoms of heroin. In contrast, D-amphetamine (1 mg/kg) was ineffective to reduce withdrawal symptoms of heroin.

The results of the present study have unexpectedly shown that mazindol, but not D-amphetamine, decreased the place preference induced by heroin and reduced the withdrawal symptoms of heroin. These results show that mazindol, but not D-amphetamine, is an effective treatment of heroin addiction by reducing both the rewarding effect and the withdrawal symptoms of heroin.

Manipulations of animals were conducted carefully in order to reduce stress at the minimum. All the experiments were performed in compliance with the guidelines of the French Ministry of Agriculture for experiments with laboratory animals (law 2013-118). The experimental protocol and euthanasia have been approved by the Ethical Committee 27, registered at the French ministry of research. Experiments were conducted during the light phase in standard conditions (T°=22.0±1.5° C.) with artificial light in quiet conditions (no noise except those generated by ventilation and by the apparatus used for experiments). The animals were not subjected to other experiments before the study. Animals were not placed in enriched environment that might modify their behavior and the effects of drugs. Each animal was identified with a bar code marked on the tail.

| Mazindol | 5-(4-Chlorophenyl)-2,5-dihydro-3H-imidazo[2,1-a]isoindol-5-ol |
|---|---|
| Vehicle | Dissolution in 0.1N HCl, then diluted with 0.9% NaCl (solution; pH 6) |
| Administration route | intra-peritoneal (i.p.) |
| Doses studied (mg/kg) | 0.125, 0.25, 0.5, 1.2 |
| Correction factor (e.g. salt/base ratio) | 1 |
| Number of administration | 1 |
| Application volume | 10 (mice) or 2 (rats) ml/kg of body weight. |
| Preparation | The solutions were prepared every week |
| Storage conditions | During tests: less than 4 h, ambient temperature (22-23° C.), protect from light Between tests 4° C., protect from light |
| PH | 6 |
| Appearance of solution | Clear, colourless, completely dissolved. |

-continued

| Methylphenidate | Methylphenidate hydrochloride |
|---|---|
| Supplier | Sigma, France |
| Vehicle | Dissolved in 0.9% NaCl |
| Administration route | i.p. |
| Doses studied (mg/kg) | 0.25, 0.5, 1, 2 |
| Correction factor (salt/base ratio) | 1 (dose expressed as salt) |
| Number of administration | 1 |
| Application volume | 10 ml/kg of body weight. |
| Preparation | The solutions are prepared extemporaneously |
| Storage conditions | Less than 4 h, ambient temperature (22-23° C.), protect from light |
| pH | 6 |
| Appearance of solution | Clear, colourless, completely dissolved. |

| D-anlphetamine | D-amphetamine sulfate |
|---|---|
| Supplier | Sigma, France |
| Code number | A5880 |
| Batch number | 058K3350 |
| Vehicle | Dissolved in 0.9% NaCl |
| Administration route | i.p. |
| Doses studied (mg/kg) | 0.125. 0.25, 0.5, 1 |
| Correction factor (salt/base ratio) | 1 (dose expressed as salt) |
| Number of administration | 1 |
| Application volume | 10 ml/kg of body weight. |
| Preparation | The solutions are prepared extemporaneously |
| Storage conditions | Less than 4 h, ambient temperature (22-23° C.), protect from light |
| pH | 6 |
| Appearance of solution | Clear, colourless, completely dissolved. |

| Heroin | |
|---|---|
| Supplier | Sigma, France |
| Vehicle | Dissolution in 0.9% NaCl |
| Administration route | i.p. |
| Doses studied (mg/kg) | 1.25, 2.5, 5 mg/kg (mice, CPP test); 3, 6, 9, 12, 15, 18, 21, 24, 27, 30 mg/kg (rats, withdrawal test) |
| Correction factor (e.g. salt/base ratio) | 1 |
| Number of administration | 4 (mice, CPP test), 25 (rats, withdrawal test) |
| Application volume | 10 (mice) or 1 (rats) ml/kg of body weight. |
| Preparation | The solutions are prepared extemporaneously |
| Storage conditions | Less than 4 h, ambient temperature (22-23° C.), protect from light |
| pH | 6 |
| Appearance of solution | Clear, colourless, completely dissolved. |

Effects of Mazindol (0.125-0.5 mg/kg) and of D-Amphetamine (0.5 mg/kg) on the Place Preference Induced by Heroin and Determination of the Place Preference Induced by Mazindol (2 mg/kg)

The experimental design is shown in Table 1. Following the habituation session (on day 1), animals (N=72) were pseudo-randomly assigned to two groups, a Control group (N=12) and a Heroin group (N=60), in a way that there was no significant difference between the two groups for the total distance travelled in the apparatus and for the percentage of time spent and the percentage distance travelled in the grey compartment and in the striped compartment.

Animals received the following treatments immediately before drug sessions:
  Control group: vehicle
  Heroin group: heroin (1.25 mg/kg)

Following the last conditioning session, the Heroin group was pseudo-randomly divided into 5 groups (N=12/group) in a way that there was no significant difference between groups for the total distance travelled in the apparatus and for the percentage of time spent and the percentage distance travelled in the grey compartment and in the striped compartment in habituation session, for the distance travelled in the drug-paired and in the vehicle-paired compartments in conditioning sessions and for the proportion of striped drug-paired compartments.

Animals received the following treatments before preference session:
Control group: vehicle of mazindol, i.p. 60 min before testing.
Hero group: vehicle of mazindol, i.p. 60 min before testing.
Hero-A 0.5 group: D-amphetamine (0.5 mg/kg), i.p. 30 min before testing.
Hero-Mz 0.125 group: mazindol (0.125 mg/kg), i.p. 60 min before testing.
Hero-Mz 0.25 group: mazindol (0.25 mg/kg), i.p. 60 min before testing.
Hero-Mz 0.5 group: mazindol (0.5 mg/kg), i.p. 60 min before testing.

TABLE 1 treatments (in mg/kg) administered in each session
(Maz: mazindol, D-A: D-amphetamine). Within
each group, drug sessions were conducted on even
sessions and vehicle sessions were conducted on odd sessions
for half of animals and vice versa for the other half of animals.

| | | Days | | | | | | | | | |
|---|---|---|---|---|---|---|---|---|---|---|---|
| | | d01 Habituation sess. | d02 | d03 | d04 | d05 | d08 | d09 | d10 | d11 | d12 Preference session |
| Group | N | | S1 | S2 | S3 | S4 | S5 | S6 | S7 | S8 | |
| Control | 12 | No treatment | Drug sessions: vehicle/ Veh sessions: vehicle | | | | | | | | Vehicle |
| Hero | 12 | | Drug/sessions: heroin 1.25 Vehicle sessions: vehicle | | | | | | | | Vehicle |
| Hero-A 0.5 | 12 | | | | | | | | | | D-A 0.5 |
| Hero-Mz 0.125 | 11 | | | | | | | | | | Mar 0.125 |
| Hero-Mz 0.25 | 12 | | | | | | | | | | Mar 0.25 |
| Hero-Mz 0.5 | 12 | | | | | | | | | | Maz 0.5 |

Effects of Mazindol (1, 2 mg/kg) and of D-Amphetamine (1 mg/kg) on the Place Preference Induced by Heroin.

The experimental design is shown in Table 2. Following the habituation session (on day 1), animals (N=72) were pseudo-randomly assigned to three groups, a Control group (N=12), a Heroin group (N=48) and a Mazindol group (N=12), in a way that there was no significant difference between the three groups for the total distance travelled in the apparatus and for the percentage of time spent and the percentage distance travelled in the grey compartment and in the striped compartment.

Animals received the following treatments before drug sessions:
Control group: vehicle, i.p. immediately before session.
Heroin group: heroin (1.25 mg/kg), i.p. immediately before session.
MAZ 2 group: mazindol (2 mg/kg), i.p. 60 min before session.

Following the last conditioning session, the Heroin group was pseudo-randomly divided into 4 groups (N=12/group) in a way that there is no significant difference between groups for the total distance travelled in the apparatus and for the percentage of time spent and the percentage distance travelled in the grey compartment and in the striped compartment in habituation session, for the distance travelled in the drug-paired and in the vehicle-paired compartments in conditioning sessions and for the proportion of striped drug-paired compartments.

Animals received the following treatments before preference session:
Control group: vehicle of mazindol, i.p. 60 min before testing.
Hero group: vehicle of mazindol, i.p. 60 min before testing.
Hero-Mz 1 group: mazindol (1 mg/kg), i.p. 60 min before testing.
Hero-Mz 2 group: mazindol (2 mg/kg), i.p. 60 min before testing.
Hero-A 1 group: D-amphetamine (1 mg/kg), i.p. 30 min before testing.
MAZ 2 group: vehicle of mazindol, i.p. 60 min before testing.

TABLE 2 treatments (in mg/kg) administered in each session.
Within each group, drug sessions were conducted on even
sessions and vehicle sessions were conducted on odd sessions
for half of animals and vice versa for the other half of animals.

| | | Days | | | | | | | | | |
|---|---|---|---|---|---|---|---|---|---|---|---|
| | | d01 Habituation session | d02 | d03 | d04 | d05 | d08 | d09 | d10 | d11 | d12 Preference session |
| Group | N | | S1 | S2 | S3 | S4 | S5 | S6 | S7 | S8 | |
| Control | 12 | No treatment | Drug sessions: vehicle/ Veh sessions: vehicle | | | | | | | | Vehicle |
| Hero | 12 | | Drug sessions: heroin 1.25 Vehicle sessions: vehicle | | | | | | | | Vehicle |
| Hero-Mz 1 | 12 | | | | | | | | | | Mazindol 1 |
| Hero-Mz 2 | 12 | | | | | | | | | | Mazindol 2 |
| Hero-A1 | 12 | | | | | | | | | | D-amphet 1 |
| MAZ 2 | 12 | | Drug sessions: mazindol 2/ Veh sessions: vehicle | | | | | | | | Vehicle |

Naloxone Precipitated Withdrawal Syndrome of Heroin

In the protocol planned before, it was planned to follow the method used by Jiang et al. Mice had to receive two subcutaneous injections/day of heroin at increasing doses (3 to 30 mg/kg) for 9 consecutive days and a single injection on the 10$^{th}$ day. This procedure led to a substantial mortality from the first days of treatment. It is likely that the discrepancy of toxicity between our experiments and the study of Jiang et al. partly resulted from difference in purity of heroin. Therefore, it was necessary to develop a method allowing to observe clear withdrawal symptoms and an acceptable mortality rate. This method is presented below. For information, 178 rats, including those used for the development of the method, have been used for this study of which 54 have been included in the results presented here.

Animals were subdivided into two groups. One group received heroin two i.p. injections/day for 12 consecutive days and a single injection on the 13$^{th}$ day (total: 25 injections) as exposed in Table 3 group received saline instead of heroin following the same protocol.

TABLE 3 doses of heroin administered i.p. from day 1 until day 13

|  | 2 injections/day at 9 pm and 17 pm | | | | | | | | | | | | 1 injection (9-11 pm) |
|---|---|---|---|---|---|---|---|---|---|---|---|---|---|
| Days | d1 | d2 | d3 | d4 | d5 | d6 | d7 | d8 | d9 | d10 | d11 | d12 | d13 |
| Doses (mg/kg) | 2 | 3 | 3 | 5 | 5 | 7 | 7 | 9 | 9 | 11 | 13 | 15 | 15 |

On day 13, animals received treatments and were tested according to the following time schedule:
T=0: i.p. injection of heroin (15 mg/kg) or vehicle.
T=2.5 h: animals individually placed in a transparent Plexiglas observation boxes (40×40×40 cm).
T=3.5 h: i.p. injection of treatment (see below).
T=4 h: i.p. injection of naloxone (5 mg/kg), start of test: observation of withdrawal symptoms as indicated in Table 4.
T=5 h: end of test, animals placed back into their home cages.

Animals received the following treatments at T 3.5 h (i.e. 30 min before injection of naloxone and observation of symptoms):
1) Animals treated with saline during the intoxication period (days 1-12) and at T0 on day 13:
   Saline group (N=8): saline (0.9% NaCl).
2) Animals treated with morphine during the intoxication period (days 1-12) and at T0 on day 13:
   Hero group (N=14): saline (0.9% NaCl).
   Amph 1 group (N=4): D-amphetamine (1 mg/kg).
   Maz 0.125 group (N=5): mazindol (0.125 mg/kg).
   Maz 0.25 group (N=6): mazindol (0.25 mg/kg).
   Maz 0.5 group (N=6): mazindol (0.5 mg/kg).
   Maz 1 group (N=6): mazindol (1 mg/kg).
   Maz 2 group (N=5): mazindol (2 mg/kg).

The withdrawal symptoms recorded are presented in Table 4. A weighting factor was ascribed for each sign from which a score was calculated.
Examples:
Body weight before naloxone injection=241 g; after naloxone injection=236 g:
   Weight loss score=2=100×(241−236)/241
Number of escape attempts=8:
   Score for escape attempts=2
Profuse salivation present:
   Score for profuse salivation
A global withdrawal score was then calculated:
Global score=the sum of the scores

TABLE 4

Withdrawal symptoms recorded and Gellert-Holtzman rating scores (11)

| Symtoms | Number of frequency of measures | Units | Weighting factor |
|---|---|---|---|
| Graded signs | | | |
| Weight loss | Body weight is measured before and 2.5 h after naloxone injection | for each 1% weight lost | 1 |
| Nb of escape attempts | counted on the six 10-min periods | 2-4 | 1 |
|  |  | 5-9 | 2 |
|  |  | 10 or more | 3 |

TABLE 4-continued

Withdrawal symptoms recorded and Gellert-Holtzman rating scores (11)

| Symtoms | Number of frequency of measures | Units | Weighting factor |
|---|---|---|---|
| Nb of abdominal constrictions |  | Each one | 2 |
| Nb of wet dog shakes |  | 1-2 | 2 |
|  |  | 3 or more | 4 |
| Checked signs-Noted simply as being presented or absent | | | |
| Diarrhea | Counted once during the whole 60-min session | If present | 2 |
| Facial Fasciculations or teeth chattering |  | If present | 2 |
| Swallowing movements |  | If present | 2 |
| Profuse salivation |  | If present | 7 |
| Chromodacryorrhea |  | If present | 5 |
| Ptosis |  | If present | 2 |
| Abnormal posture |  | If present | 3 |
| Erection or ejaculation |  | If present | 3 |
| Irritability |  | If present | 3 |

Effects of Mazindol and of D-Amphetamine on the Place Preference Induced by Heroin and Determination of the Place Preference Induced by Mazindol The results of the preference session are presented in Table 5.

Effect of Heroin

Figure 2:
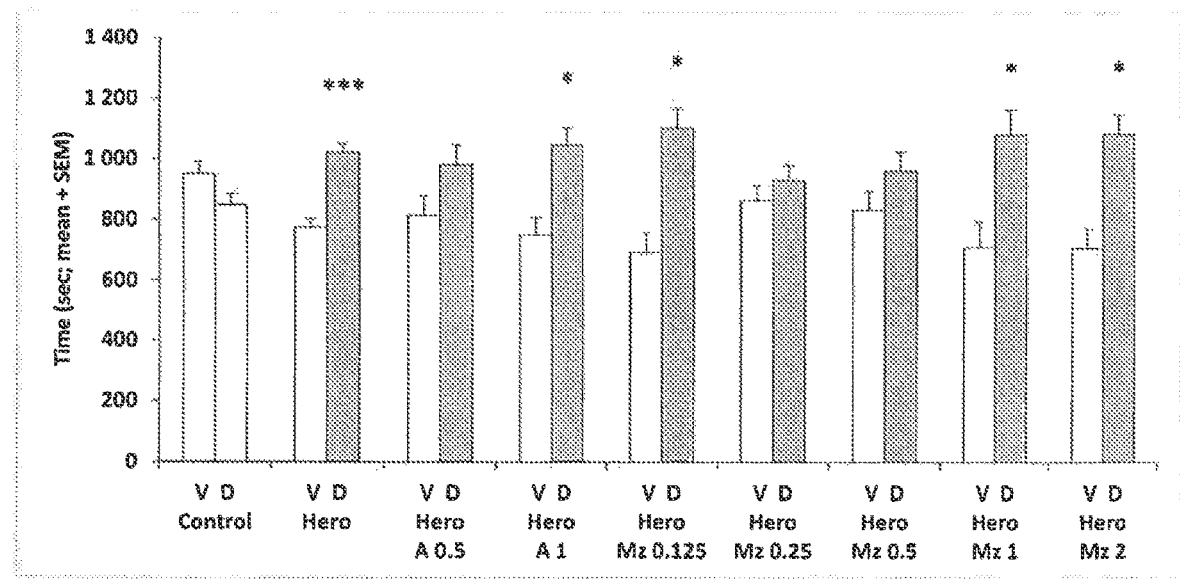
FIG. 2 shows (higher panel) and compares (lower panel) the time spent in the vehicle-paired and in the drug-paired (D) compartment after administration with a control, mazindol or amphetamine in mice.
Figure 2:
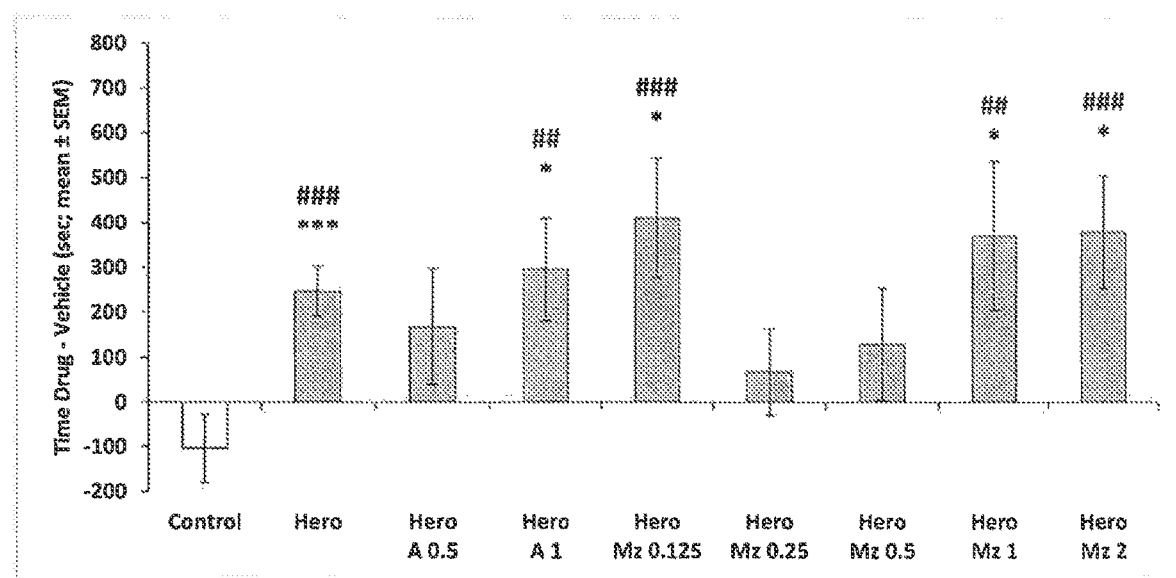
Figure 3:
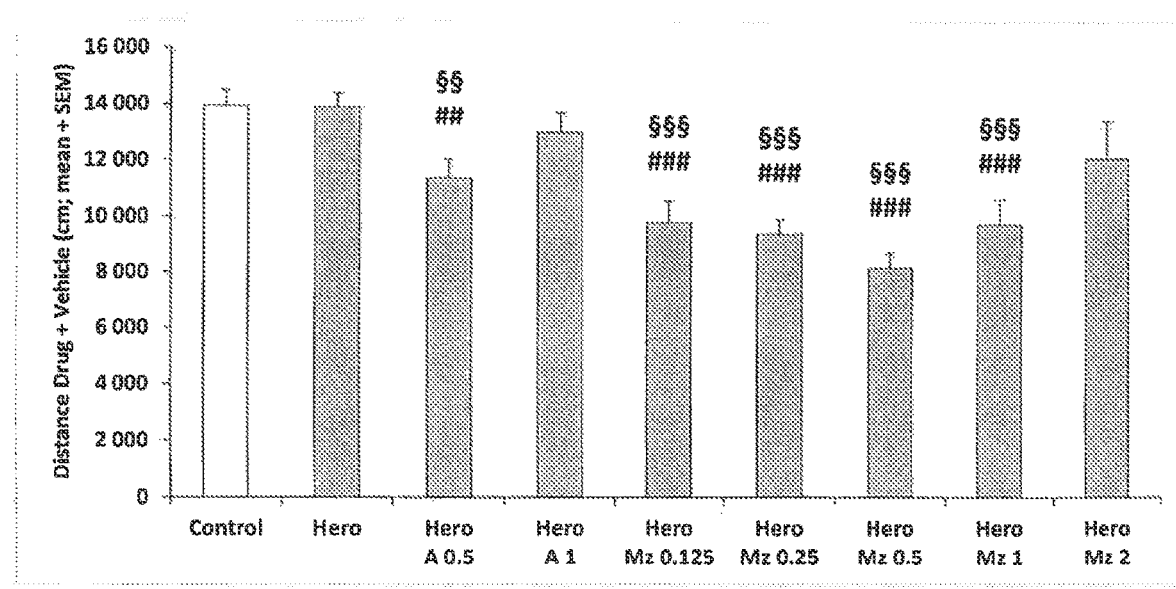
FIG. 3 shows the total distance travelled in both vehicle-paired (V) and drug-paired (D) compartments after administration with a control, mazindol or amphetamine in mice.

Heroin (1.25 mg/kg), administered before drug sessions induced the same effects at the preference session.
An increase of the difference of distance travelled in the drug-paired vs. the vehicle-paired compartment:
   In the Hero group, but not in the Control group, the distance travelled was higher in the drug-paired compartment than in the vehicle-paired compartment (FIG. 1, upper panel).
   The difference of distance travelled in the drug-paired vs. the vehicle-paired compartment was higher in the Hero group than in the Control group (FIG. 1, lower panel).
An increase of the time spent in the drug-paired vs. the vehicle-paired compartment:
   In the Hero group, but not in control group, the time spent was higher in the drug-paired compartment than in the vehicle-paired compartment (FIG. 2, upper panel).
   The difference of time spent in the drug-paired vs. the vehicle-paired compartment was higher in the Hero group than in the Control group (FIG. 2, lower panel).
No significant modification of the total distance travelled in two compartments (FIG. 3).
Conclusions: Heroin (1.25 mg/kg) induced a place preference.

Heroin (1.25 mg/kg) dramatically increased the distance travelled in the drug-paired compartment comparatively with the vehicle-paired compartment at the preference session and more modestly but significantly increased the time spent in the drug-paired compartment.

Effect of D-Amphetamine on Place Preference Induced by Heroin

D-amphetamine (0.5, 1 mg/kg) administered before the preference session induced the following effects:
   D-amphetamine did not significantly modify the difference of distance travelled in the drug-paired vs. the vehicle-paired compartment:

In the two Hero-A groups, the distance travelled was higher in the drug-paired compartment than in the vehicle-paired compartment (FIG. 1, upper panel).

The difference of distance travelled in the drug-paired vs. the vehicle-paired compartment was higher in the two Hero-A groups than in the Control group and not significantly different between Hero-A groups and the Hero group (FIG. 1, lower panel).

D-amphetamine at 0.5 mg/kg, but not at 1 mg/kg, tended to decrease the time spent in the drug-paired compartment:

In the Hero-A 0.5 group:
The time spent was not significantly different between the drug-paired and the vehicle-paired compartment (FIG. 2, upper panel).
The difference of time spent in the drug-paired vs. the vehicle-paired compartment was not significantly different from both the Control group and the Hero group (FIG. 2, lower panel).

In the Hero-A 1 group:
The time spent was higher in the drug-paired compartment than in the vehicle-paired compartment (FIG. 2, upper panel).
The difference of time spent in the drug-paired vs. the vehicle-paired compartment was higher than in the Control group and not significantly different between from Hero group (FIG. 2, lower panel).

D-amphetamine at 0.5 mg/kg, but not at 1 mg/kg decreased the total distance travelled in two compartments (FIG. 3).

Conclusions: These results do not show a reliable effect of D-amphetamine on the place preference induced by heroin.

D-amphetamine (0.5 mg/kg) non-significantly reduced the heroin-induced increase of time spent in the drug-paired compartment and had no effect on the heroin-induced increase of distance travelled in the drug-paired compartment.

D-amphetamine (1 mg/kg) did not modify the heroin-induced increases of time spent and distance travelled in the drug-paired compartment.

Effect of Mazindol on Place Preference Induced by Heroin

Mazindol (0.125, 025, 0.5, 1 and 2 mg/kg) administered before the preference session induced the following effects:

Mazindol (0.125 mg) had no significant effect on the heroin-induced increases of distance travelled (FIG. 1 and of time spent (FIG. 2) in the drug-paired compartment.

Mazindol (0.25 mg/kg):
Significantly reduced the heroin-induced increase of the difference of distance travelled in the drug-paired vs. in the vehicle-paired compartment (FIG. 1, lower panel), but this effect was partial, since the Hero-Mz 0.25 group travelled more distance in the drug-paired than in the vehicle-paired compartment (FIG. 1, higher panel).
Tended to reduce the heroin-induced increase of time spent in the drug-paired compartment: the time spent by the Hero-Mz 0.25 group was not significantly different between the drug paired and the vehicle-paired compartment (FIG. 2, higher panel), was not significantly different from the Control group but was also not significantly different from the Heroin group (FIG. 2, lower panel).

Mazindol (0.5 mg/kg):
Significantly antagonized the heroin-induced increase of the difference of distance travelled in the drug-paired vs. in the vehicle-paired compartment: in the Hero-Mz 0.5 group, the distance travelled was not significantly different between the drug-paired and the vehicle-paired compartment (FIG. 1, higher panel), and the difference of distance travelled in the drug-paired vs. in the vehicle-paired compartment was lower than the Hero group and not significantly different between from the Control group (FIG. 1, lower panel).
Tended to reduce the heroin-induced increase of time spent in the drug-paired compartment: the time spent by the Hero-Mz 0.5 group was not significantly different between the drug-paired and the vehicle-paired compartment (FIG. 2, higher panel), was not significantly different from the Control group but was also not significantly different from the Heroin group (FIG. 2, lower panel).

Mazindol (1 mg/kg):
Did not significantly reduce the heroin-induced increase of the difference of distance travelled in the drug-paired vs. in the vehicle-paired compartment: in the Hero-Mz 1 group, the distance travelled tended (p=0.06) to be higher the drug-paired and the vehicle-paired compartment (FIG. 1, higher panel), and the difference of distance travelled in the drug-paired vs. in the vehicle-paired compartment was not significantly different from the Hero group and was higher than the Control group (FIG. 1, lower panel).
Did not significantly modify the heroin-induced increase of time spent in the drug-paired compartment (FIG. 2).

Mazindol (2 mg) had no significant effect on the heroin-induced increases of distance travelled (FIG. 1) and of time spent (FIG. 2) in the drug-paired compartment.

Mazindol decreased locomotor activity at all doses tested except 2 mg/kg (FIG. 3)

Conclusions. These results show that mazindol (0.25, 0.5 mg/kg) decreased the place preference induced by heroin.

The heroin-induced increase of distance travelled in the drug-paired compartment was reduced by mazindol (0.25 mg/kg) and was antagonized by mazindol (0.5 mg/kg). The distance travelled was not significantly different between the drug-paired and the vehicle paired compartment in animals treated with mazindol (0.5 mg/kg), and there was no significant difference of time spent in the drug-paired compartment vs. the vehicle-paired compartment in animals treated with mazindol (0.25, 0.5 mg/kg). Mazindol (0.125, 1 and 2 mg/kg) did not induce modifications of the distance travelled and time spent in the drug-paired vs. the vehicle-paired compartments, and therefore did not induce effects suggesting a decrease of the place preference induced by heroin.

TABLE 5

Distance travelled in the two compartments, in the vehicle-paired compartment, in the drug-paired compartment and in the drug-paired compartment minus the vehicle paired compartment and time spent in the vehicle-paired compartment, in the drug-paired compartment and in the drug-paired compartment minus the vehicle paired compartment at the preference session. Statistical analysis. "p drug vs. vehicle": within each individual group, p values for the comparisons of the distance travelled and of the time spent in the drug-paired compartment vs. the vehicle-paired compartment (two-tailed paired Student's). "p vs. Control" and "p vs. Hero": comparison vs. the Control group and vs. the Heroin group, respectively, of the total distance travelled and of the differences of distance travelled and of time spent between the drug-paired compartment and the vehicle-paired compartment, of Heroin groups vs. the Control group (two-tailed unpaired Student's t test).

| | | Day 12 - Preference session | | | | | | |
|---|---|---|---|---|---|---|---|---|
| | | Distance (cm) | | | | Time (sec) | | |
| | | Drug + | Compartment | | | Compartment | | |
| Group | | Vehicle | Vehicle | Drug | Drug-Vehicle | Vehicle | Drug | Drug-Vehicle |
| Control | Mean | 13942.1 | 7220.9 | 6721.2 | −499.6 | 951.7 | 848.3 | −103.5 |
| N = 24 | SEM | 550.5 | 336.4 | 365.9 | 437.1 | 38.1 | 38.1 | 76.2 |
| p drug vs. vehicle ≤ | | | | 0.265 | | | 0.188 | |
| Hero | Mean | 13892.0 | 5948.4 | 7943.6 | 1995.3 | 776.3 | 1023.7 | 247.4 |
| N = 24 | SEM | 499.5 | 322.9 | 274.6 | 331.5 | 27.9 | 27.9 | 55.8 |
| p drug vs. vehicle ≤ | | | | 0.001 | | | 0.001 | |
| p vs. Control ≤ | | 0.947 | | | 0.001 | | | 0.001 |
| Hero-A 0.5 | Mean | 11379.9 | 4582.7 | 6797.2 | 2214.6 | 815.5 | 984.5 | 168.9 |
| N = 11 | SEM | 662.9 | 326.4 | 410.9 | 333.6 | 64.6 | 64.6 | 129.3 |
| p drug vs. vehicle ≤ | | | | 0.001 | | | 0.221 | |
| p vs. Control ≤ | | 0.010 | | | 0.001 | | | 0.064 |
| p vs. Hero ≤ | | 0.006 | | | 0.688 | | | 0.516 |
| Hero-A 1 | Mean | 13005.6 | 5588.9 | 7416.7 | 1827.8 | 751.7 | 1048.3 | 296.5 |
| N = 12 | SEM | 677.8 | 330.7 | 553.2 | 609.3 | 57.6 | 57.6 | 115.1 |
| p drug vs. vehicle ≤ | | | | 0.012 | | | 0.026 | |
| p vs. Control ≤ | | 0.314 | | | 0.004 | | | 0.006 |
| p vs. Hero ≤ | | 0.307 | | | 0.794 | | | 0.667 |
| Hero-Mz 0.125 | Mean | 9800.4 | 4176.5 | 5623.8 | 1447.3 | 694.3 | 1105.7 | 411.3 |
| N = 11 | SEM | 764.5 | 418.2 | 435.1 | 379.3 | 66.4 | 66.4 | 132.8 |
| p drug vs. vehicle ≤ | | | | 0.003 | | | 0.011 | |
| p vs. Control ≤ | | 0.001 | | | 0.009 | | | 0.001 |
| p vs. Hero ≤ | | 0.001 | | | 0.330 | | | 0.186 |
| Hero-Mz-0.25 | Mean | 9390.5 | 4298.4 | 5092.1 | 793.8 | 866.1 | 933.9 | 67.8 |
| N = 12 | SEM | 518.8 | 266.0 | 335.6 | 312.5 | 48.7 | 48.7 | 97.4 |
| p drug vs. vehicle ≤ | | | | 0.027 | | | 0.501 | |
| p vs. Control ≤ | | 0.001 | | | 0.058 | | | 0.190 |
| p vs. Hero ≤ | | 0.001 | | | 0.027 | | | 0.095 |
| Hero-Mz 0.5 | Mean | 8164.5 | 3752.8 | 4411.7 | 659.0 | 834.9 | 965.1 | 130.1 |
| N = 11 | SEM | 557.0 | 246.6 | 377.2 | 309.8 | 62.8 | 62.8 | 125.5 |
| p drug vs. vehicle ≤ | | | | 0.059 | | | 0.324 | |
| p vs. Control ≤ | | 0.001 | | | 0.099 | | | 0.107 |
| p vs. Hero ≤ | | 0.001 | | | 0.018 | | | 0.326 |
| Hero-Mz 1 | Mean | 9746.4 | 4281.9 | 5464.5 | 1182.6 | 714.0 | 1086.0 | 372.0 |
| N = 12 | SEM | 879.3 | 458.4 | 597.7 | 601.3 | 83.2 | 83.2 | 166.4 |
| p drug vs. vehicle ≤ | | | | 0.075 | | | 0.047 | |
| p vs. Control ≤ | | 0.001 | | | 0.032 | | | 0.005 |
| p vs. Hero ≤ | | 0.001 | | | 0.207 | | | 0.382 |
| Hero-Mz 2 | Mean | 12086.8 | 5047.9 | 7038.9 | 1990.9 | 710.3 | 1089.7 | 379.3 |
| N = 12 | SEM | 1332.9 | 604.6 | 761.2 | 336.6 | 62.4 | 62.4 | 124.8 |
| p drug vs. vehicle ≤ | | | | 0.001 | | | 0.011 | |
| p vs. Control ≤ | | 0.136 | | | 0.001 | | | 0.001 |
| p vs. Hero ≤ | | 0.132 | | | 0.994 | | | 0.271 |

Determination of the Place Preference Induced by Mazindol

The results of the preference session are presented in Table 6.

Figure 7:
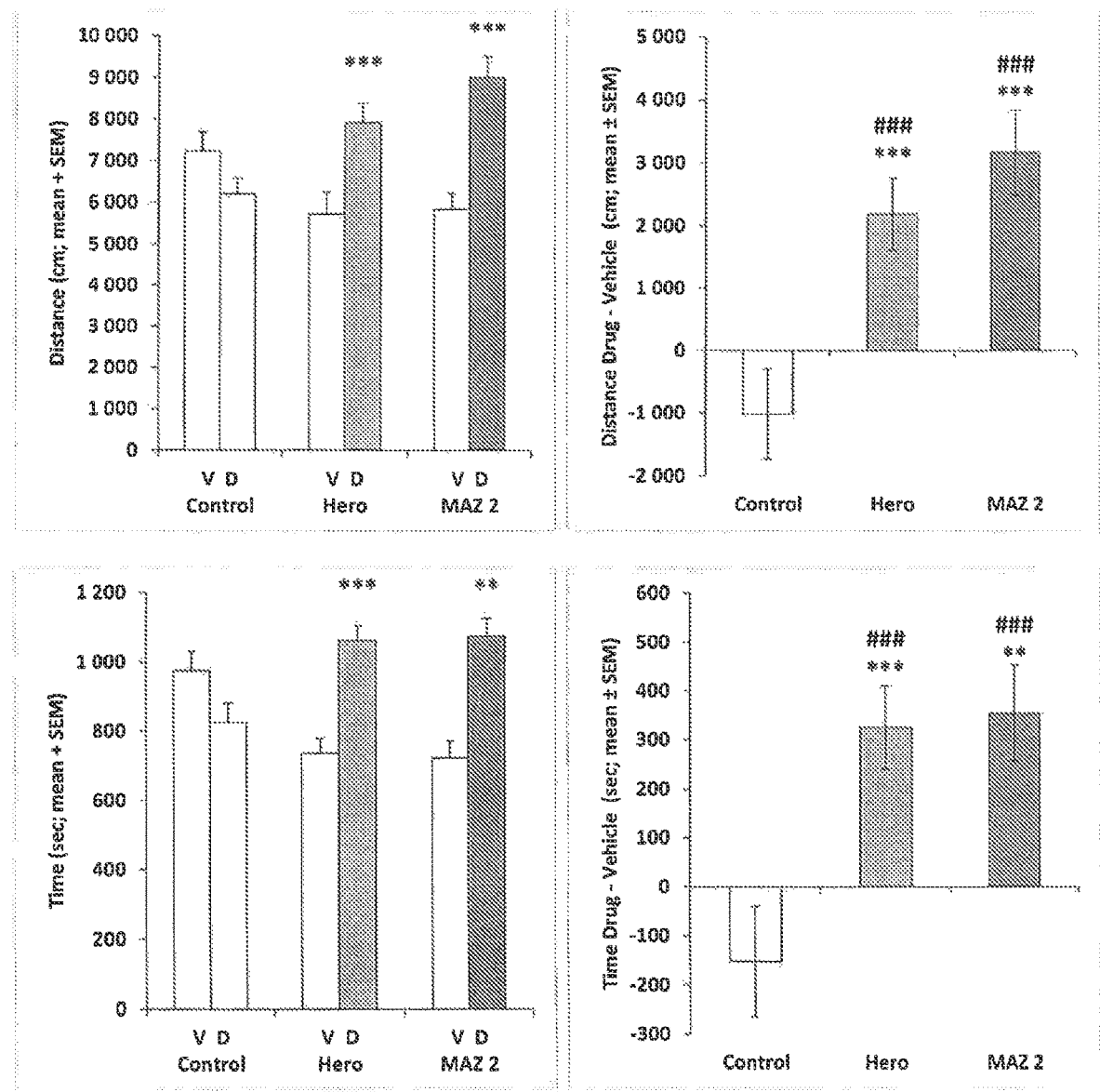
FIG. 7 shows (top left panel) and compares (top right panel) the distance travelled in the vehicle-paired (V) and in the drug-paired (D) compartment (left panel) after administration with a control, heroin or mazindol in mice. The lower panel shows (lower left panel) and compares (lower right panel) the time spent in the vehicle-paired (V) and in the drug-paired (D) compartment after administration with a control, heroin or mazindol in mice.

Mazindol (2 mg/kg), administered before drug sessions induced the following effects at the preference session:

An increase of the difference of distance travelled in the drug-paired vs. the vehicle-paired compartment:

In the MAZ 2 group, as well as in the Hero group, but not in the Control group, the distance travelled was higher in the drug-paired compartment than in the vehicle-paired compartment (FIG. 7, upper left panel).

The difference of distance travelled in the drug-paired vs. the vehicle-paired compartment was higher in the MAZ 2 group than in the Control group and was not significantly different between the MAZ 2 and the Hero group (FIG. 7, upper right panel).

An increase of the time spent in the drug-paired vs. the vehicle-paired compartment:

In the MAZ 2 group, as well as in the Hero group, but not in control group, the time spent was higher in the drug-paired compartment than in the vehicle-paired compartment (FIG. 7, lower left panel).

The difference of time spent in the drug-paired vs. the vehicle-paired compartment was higher in the MAZ 2 group than in the Control group and was not significantly different between the MAZ 2 and the Hero group (FIG. 7, lower right panel).

Conclusions. Mazindol (2 mg/kg) induced a place preference.

Mazindol (2 mg/kg) dramatically increased the distance travelled and the time spent in the drug-paired compartment comparatively with the vehicle-paired compartment at the preference session. These effects were of the same extent as those induced by heroin (1.25 mg/kg).

Figure 5:
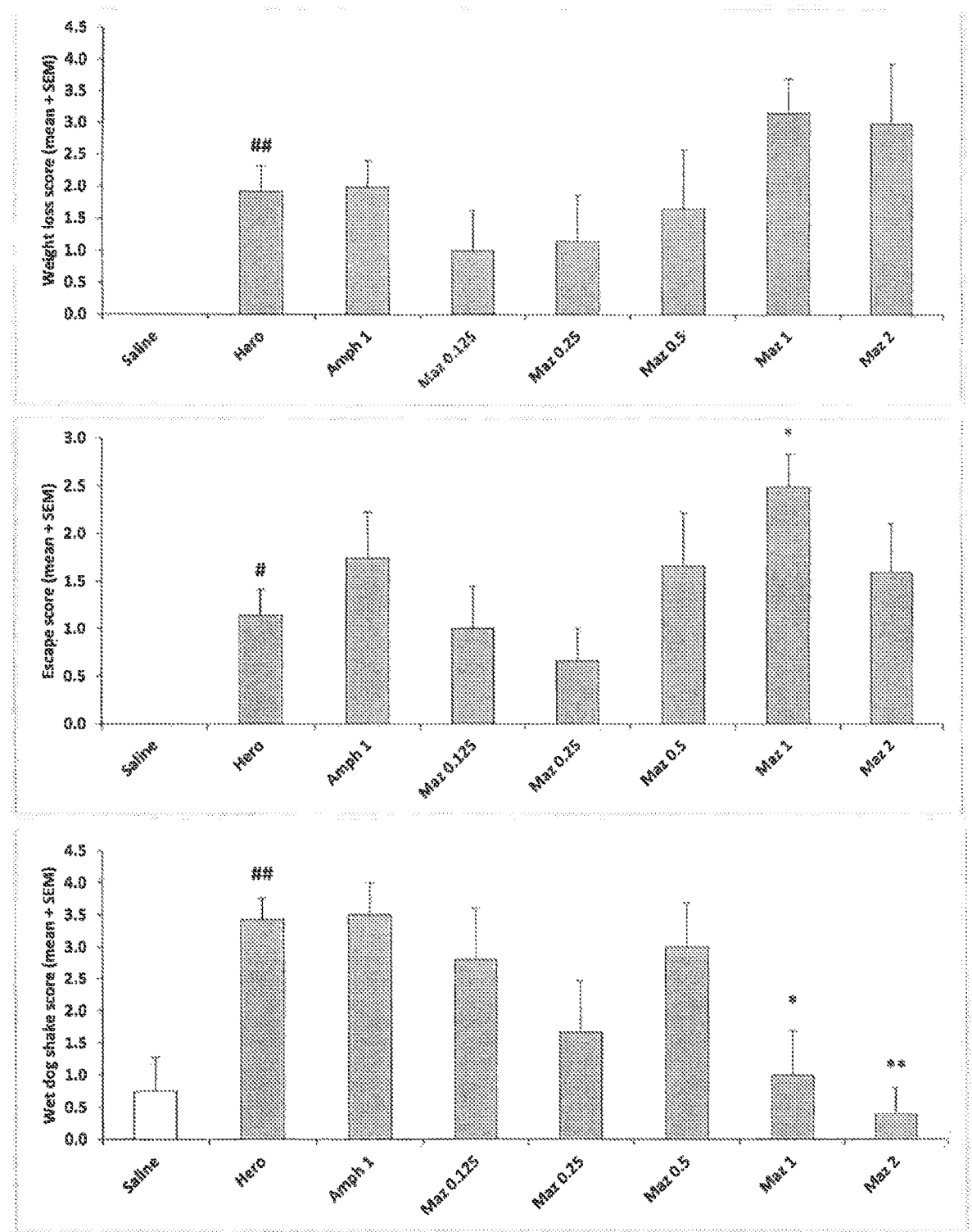
FIG. 5 shows scores for weight loss (upper panel), for escape attempts (middle panel) and for wet dog shakes (lower panel) after administration with a control, mazindol or amphetamine in rats subjected to Naloxone precipitated withdrawal syndrome of heroin.
Figure 6:
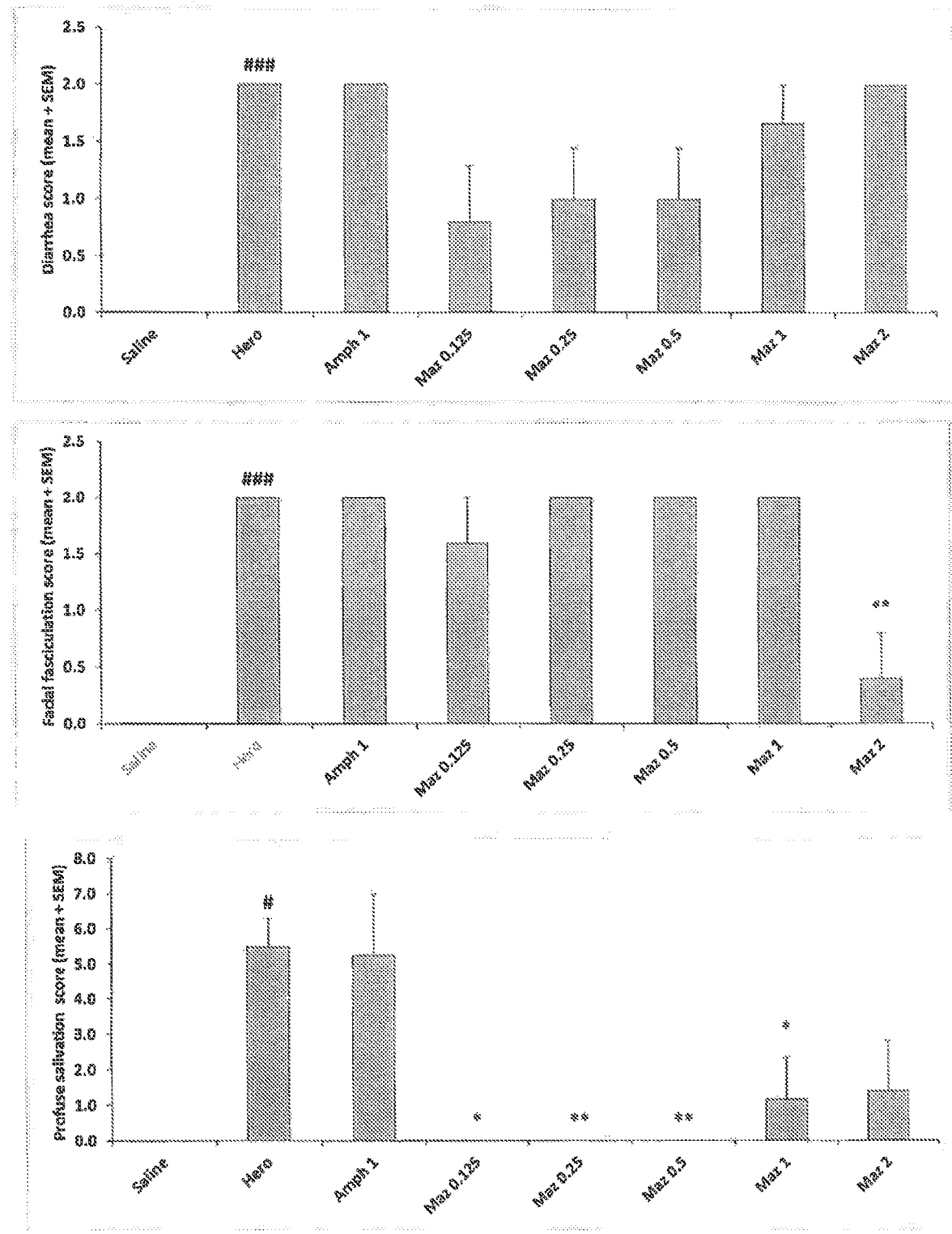
FIG. 6 shows scores for diarrhea (upper panel), facial fasciculation or teeth chattering (middle panel) and profuse salivation (lower panel) after administration with a control, mazindol or amphetamine in rats subjected to Naloxone precipitated withdrawal syndrome of heroin.

D-amphetamine (1 mg/kg) did not reduce the global score (FIG. 4) and the different withdrawal symptoms (FIG. 5) (FIG. 6). Conversely, D-amphetamine tended to increase on symptom, the chromodacryorrhea. This increase was not significant probably because of the small number of subjects in the amphetamine group.

Figure 4:
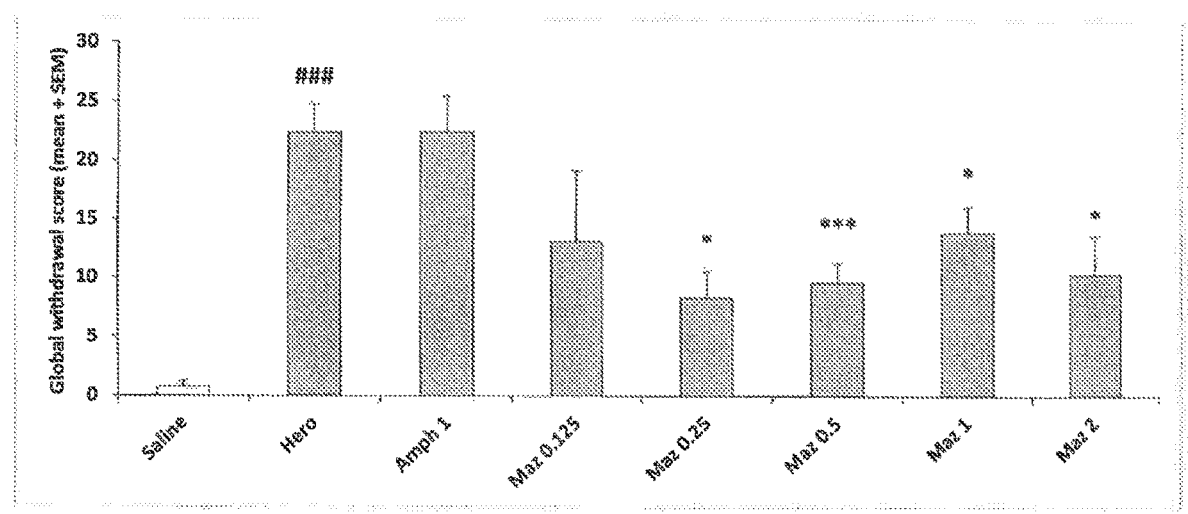
FIG. 4 shows the overall global score of withdrawal symptoms after administration with a control, mazindol or amphetamine in rats subjected to Naloxone precipitated withdrawal syndrome of heroin.

Mazindol:
Reduced the global score; this effect was significant at all doses except 0.125 mg/kg (FIG. 4).
Reduced the scores for wet dog shake (significant effect at 1 and 2 mg/kg) (FIG. 5) facial fasciculation or teeth chattering (significant at 2 mg/kg) and profuse salivation (significant at all doses except 2 mg/kg) (FIG. 6).
Did not significantly reduce the scores for weight loss and escape attempt, which was, to the contrary, increased by mazindol (2 mg/kg) (FIG. 5) and diarrhea (FIG. 6).

TABLE 6

Distance travelled in the two compartments, in the vehicle-paired compartment, in the drug-paired compartment and in the drug-paired compartment minus the vehicle paired compartment and time spent in the vehicle-paired compartment, in the drug paired compartment and in the drug-paired compartment minus the vehicle paired compartment at the preference session. Statistical analysis. "p drug vs, vehicle": within each individual group, p values for the comparisons of the distance travelled and of the time spent in the drug-paired compartment vs. the vehicle-paired compartment (two-tailed paired Student's). "p vs Control" and "p vs. Hero": comparison vs, the Control group and vs. the Heroin group, respectively, of the total distance travelled and of the differences of distance travelled and of time spent between the drug-paired compartment and the vehicle-paired compartment, of Heroin groups vs. the Control group (two-tailed unpaired Student's t test).

| | | Day 12—Preference session | | | | | |
|---|---|---|---|---|---|---|---|
| | | | Distance (cm) | | | Time (sec) | |
| | | Drug + | Compartment | | Drug- | Compartment | Drug- |
| Group | | Vehicle | Vehicle | Drug | Vehicle | Vehicle | Drug | Vehicle |
| Control | Mean | 13431.6 | 7225.3 | 6206.4 | −1018.9 | 975.8 | 824.2 | −151.5 |
| N = 12 | SEM | 423.6 | 459.3 | 373.1 | 721.7 | 56.0 | 56.0 | 112.0 |
| p drug vs. vehicle ≤ | | | | 0.186 | | | 0.203 | |
| Hero | Mean | 13647.5 | 5728.4 | 7919.1 | 2190.6 | 737.0 | 1063.0 | 325.9 |
| N = 12 | SEM | 815.3 | 527.5 | 465.9 | 570.9 | 41.8 | 41.8 | 83.7 |
| p drug vs. vehicl e≤ | | | | 0.001 | | | 0.001 | |
| p vs. Control ≤ | | 0.816 | | | 0.001 | | | 0.001 |
| MAZ 2 | Mean | 14858.2 | 5845.2 | 9013.0 | 3167.8 | 722.7 | 1077.3 | 354.6 |
| N = 12 | SEM | 571.5 | 383.2 | 495.4 | 678.1 | 49.1 | 49.1 | 58.2 |
| p drug vs. vehicl e≤ | | | | 0.001 | | | 0.002 | |
| p vs. Control ≤ | | 0.057 | | | 0.001 | | | 0.001 |
| p vs. Hero ≤ | | 0.237 | | | 0.282 | | | 0.826 |

Naloxone Precipitated Withdrawal Syndrome of Heroin

The results are presented in Table 7.

Heroin induced an increase of the global score (FIG. 4) and of the scores for weight loss, escape attempts, wet dog shake (FIG. 5), diarrhea, facial fasciculation or teeth chattering and profuse salivation (FIG. 6).

Heroin also non-significantly increased the scores for abdominal constrictions and chromodacryorrhea.

Conclusions. Mazindol reduced the withdrawal symptoms of heroin.

Mazindol decreased the naloxone precipitated withdrawal symptoms of heroin. This effect was significant at 0.25, 0.5, 1 and 2 mg/kg, but not at 0.125 mg/kg. D-amphetamine at 1 mg/kg did not reduce the withdrawal symptoms of heroin.

TABLE 7

Naloxone precipitated withdrawal syndrome of heroin. Statistical analysis. Difference vs. Saline group or vs. Hero group: p values (Mann-Whitney U test).

| Group | | 1. Global Score | 2. W Los | 3. Esc A | 4. Abd C | 5. W D S | 6. Diarr | 7. F F T C | 8. Sw M | 9. Pr Sal | 10. Chr | 11. Ptos | 12. Ab P | 13. Er Ej | 14. Irrit |
|---|---|---|---|---|---|---|---|---|---|---|---|---|---|---|---|
| Saline | Mean | 0.8 | 0.0 | 0.0 | 0.0 | 0.8 | 0.0 | 0.0 | 0.0 | 0.0 | 0.0 | 0.0 | 0.0 | 0.0 | 0.0 |
| n = 8 | SEM | 0.5 | 0.0 | 0.0 | 0.0 | 0.5 | 0.0 | 0.0 | 0.0 | 0.0 | 0.0 | 0.0 | 0.0 | 0.0 | 0.0 |
| Hero | Mean | 22.4 | 1.9 | 1.1 | 4.1 | 3.4 | 2.0 | 2.0 | 0.9 | 5.5 | 1.1 | 0.1 | 0.2 | 0.0 | 0.0 |

TABLE 7-continued

Naloxone precipitated withdrawal syndrome of heroin.
Statistical analysis. Difference vs. Saline group or vs.
Hero group: p values (Mann-Whitney U test).

| Group | | 1. Global Score | 2. W Los | 3. Esc A | 4. Abd C | 5. W D S | 6. Diarr | 7. F F T C | 8. Sw M | 9. Pr Sal | 10. Chr | 11. Ptos | 12. Ab P | 13. Er Ej | 14. Irrit |
|---|---|---|---|---|---|---|---|---|---|---|---|---|---|---|---|
| n = 14 | SEM | 2.4 | 0.4 | 0.3 | 2.8 | 0.3 | 0.0 | 0.0 | 0.3 | 0.8 | 0.5 | 0.1 | 0.2 | 0.0 | 0.0 |
| p vs Saline | | 0.001 | 0.002 | 0.02 | 0.5 | 0.004 | 0.001 | 0.001 | 0.2 | 0.03 | 0.5 | 0.8 | 0.8 | 1 | 1 |
| Amph 1 | Mean | 22.5 | 2.0 | 1.8 | 0.0 | 3.5 | 2.0 | 2.0 | 1.0 | 5.3 | 5.0 | 0.0 | 0.0 | 0.0 | 0.0 |
| n = 4 | SEM | 3.0 | 0.4 | 0.5 | 0.0 | 0.5 | 0.0 | 0.0 | 0.6 | 1.8 | 0.0 | 0.0 | 0.0 | 0.0 | 0.0 |
| p vs. Hero | | 0.5 | 0.8 | 0.4 | 0.6 | 1 | 1 | 1 | 0.9 | 1 | 0.06 | 0.9 | 0.9 | 1 | 1 |
| Maz 0.125 | Mean | 13.2 | 1.0 | 1.0 | 2.8 | 2.8 | 0.8 | 1.6 | 1.2 | 0.0 | 2.0 | 0.0 | 0.0 | 0.0 | 0.0 |
| n = 5 | SEM | 6.0 | 0.6 | 0.4 | 2.8 | 0.8 | 0.5 | 0.4 | 0.5 | 0.0 | 1.2 | 0.0 | 0.0 | 0.0 | 0.0 |
| p vs. Hero | | 0.2 | 0.3 | 0.9 | 1 | 0.6 | 0.06 | 0.6 | 0.6 | 0.02 | 0.6 | 0.9 | 0.9 | 1 | 1 |
| Maz 0.25 | Mean | 8.3 | 1.2 | 0.7 | 0.0 | 1.7 | 1.0 | 2.0 | 1.0 | 0.0 | 0.8 | 0.0 | 0.0 | 0.0 | 0.0 |
| n = 6 | SEM | 2.2 | 0.7 | 0.3 | 0.0 | 0.8 | 0.4 | 0.0 | 0.4 | 0.0 | 0.8 | 0.0 | 0.0 | 0.0 | 0.0 |
| p vs. Hero | | 0.02 | 0.4 | 0.4 | 0.5 | 0.08 | 0.09 | 1 | 0.9 | 0.007 | 0.9 | 0.9 | 0.9 | 1 | 1 |
| Maz 0.5 | Mean | 9.7 | 1.7 | 1.7 | 0.0 | 3.0 | 1.0 | 2.0 | 0.3 | 0.0 | 0.0 | 0.0 | 0.0 | 0.0 | 0.0 |
| n = 6 | SEM | 1.6 | 0.9 | 0.6 | 0.0 | 0.7 | 0.4 | 0.0 | 0.3 | 0.0 | 0.0 | 0.0 | 0.0 | 0.0 | 0.0 |
| p vs. Hero | | 0.001 | 0.5 | 0.4 | 0.5 | 0.7 | 0.9 | 1 | 0.4 | 0.007 | 0.7 | 0.9 | 0.9 | 0.6 | 1 |
| Maz 1 | Mean | 14.0 | 3.2 | 2.5 | 0.0 | 1.0 | 1.7 | 2.0 | 0.3 | 1.2 | 1.7 | 0.0 | 0.0 | 0.5 | 0.0 |
| n = 6 | SEM | 2.2 | 0.5 | 0.3 | 0.0 | 0.7 | 0.3 | 0.0 | 0.3 | 1.2 | 1.1 | 0.0 | 0.0 | 0.5 | 0.0 |
| p vs. Hero | | 0.03 | 0.1 | 0.02 | 0.5 | 0.02 | 0.6 | 1 | 0.4 | 0.04 | 0.7 | 0.9 | 0.9 | 0.6 | 1 |
| Maz 2 | Mean | 10.4 | 3.0 | 1.6 | 0.0 | 0.4 | 2.0 | 0.4 | 0.0 | 1.4 | 1.0 | 0.0 | 0.6 | 0.0 | 0.0 |
| n= 5 | SEM | 3.4 | 0.9 | 0.5 | 0.0 | 0.4 | 0.0 | 0.4 | 0.0 | 1.4 | 1.0 | 0.0 | 0.6 | 0.0 | 0.0 |
| p vs. Hero | | 0.02 | 0.3 | 0.5 | 0.5 | 0.005 | 1 | 0.01 | 0.2 | 0.06 | 1 | 0.9 | 0.7 | 1 | 1 |

1: global score and scores for the different symptoms,
2: weight loss,
3: escape attempts,
4: abdominal constrictions,
5: wet dog shakes,
6: diarrhea,
7: facial fasciculation or teeth chattering,
8: swallowing movements,
9: profuse salivation,
10: chromodacryorrhea,
11: ptosis,
12: abnormal posture,
13: erection or ejaculation and
14: irritability

REFERENCES (1)
(2)
(3) Bremer P T, et al.: Development of a Clinically Viable Heroin Vaccine. *J. Am. Chem. Soc.* 2016; 139(25)8601-8611.
(4) Hadler J: Mazindol, a New Non-Amphetamine Anorexigenic Agent. *J Clin Pharmacology.* 1972; 12(11):453-45.
(5) Kim S S, Lee H W, Lee K T: Validated method for determination of mazindol in human plasma by liquid chromatography/tandem mass spectrometry. *J Chromatogr B Analyt Technol Blamed Life Sci.* 2009; 877: 1011-16.
(6) Seibyl J P, et al.: Mazindol and cocaine addiction in schizophrenia. *Biol Phsychiatry.* 1992; 31:1172-1183.
(7) Stine S M, et al. Mazindol treatment for cocaine dependence. *Drug Alcohol Depend.* 1995; 39(3):245-52.
(8) Margolin A, et al. Mazindol for relapse prevention to cocaine abuse in methadone-maintained patients. *Am J Drug Alcohol Abuse.* 1995; 21(4)469-81.
(9) Schlussman S D, Zhang Y, Hsu N M, Allen J M, Ho A, Kreek M J. Heroin-induced locomotor activity and conditioned place preference in C57BL/6J and 129P3/J mice. *Neurosci Lett.* 2008; 440(3):284-8.
(10) Jiang L H, Wang J, Wei X L, Liang Q Y, Cheng T T. Exogenous sodium hydrosulfide can attenuate naloxone-precipitated withdrawal syndromes and affect cAMP signaling pathway in heroin-dependent rat's nucleus accumbens. *Eur Rev Med Pharmacol Sci.* 2012; 16(14):1974-82.
(11) Gellert V F, Holtzman S G. Development and maintenance of morphine tolerance and dependence in the rat by scheduled access to morphine drinking solutions. *J Pharmacol Exp Ther.* 1978; 205:536-546.
(12) Robeldo-Gonzalez et al. Repeated administration of mazindol reduces spontaneous pain-related behaviors without modifying bone density and microarchitecture in a mouse model of complete Freund's adjuvant-induced knee arthritis. *Journal of Pain Research* 2017: 10 1777-1786.

The invention claimed is:

1. A method of treatment of substance abuse disorder comprising administering mazindol or composition comprising mazindol to a subject, wherein the substance is an opioid and mazindol is administered daily at a daily dosage range of between 3 mg and 16 mg.

2. The method according to claim 1, wherein the substance is heroin.

3. The method according to claim 1, wherein mazindol or the composition comprising mazindol is administered via oral administration, preferably in the form of a tablet.

4. The method according to claim 3, wherein mazindol or the composition comprising mazindol is administered in the form of a tablet and the tablet comprises 1 to 6 mg of mazindol.

5. The method according to claim 1, wherein mazindol is in the form of a multilayer matrix-type tablet comprising:

at least one immediate-release (IR) layer comprising mazindol and at least one diluent, at least one sustained-release layer (SR) comprising mazindol and at least one sustained-release, pH independent and water-insoluble polymer.

6. The method according to claim 5, wherein the ratio in weight between the IR layers and the SR layers is between 40:60 and 80:20.

7. The method according to claim 5, wherein the tablet has a dissolution of between 60% and 80% at 1 hour, and of between 70% and 90% at 2 hours.

8. The method of claim 5, wherein the weight ratio ranges from 50:50 to 70:30.

9. The method of claim 5, wherein the weight ratio is 50:50.

* * * * *